US008824755B2

(12) United States Patent
Beck et al.

(10) Patent No.: US 8,824,755 B2
(45) Date of Patent: Sep. 2, 2014

(54) METHOD AND COMPUTER SYSTEM FOR AUTOMATICALLY GENERATING A STATISTICAL MODEL

(75) Inventors: Thomas Beck, Appenweler (DE); Dominik Bernhardt, Hausen (DE); Christian Godenschwager, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 135 days.

(21) Appl. No.: 13/368,395

(22) Filed: Feb. 8, 2012

(65) Prior Publication Data

US 2012/0201442 A1 Aug. 9, 2012

Related U.S. Application Data (60) Provisional application No. 61/440,989, filed on Feb. 9, 2011.

(51) Int. Cl.
| | |
|---|---|
| *G06F 9/00* | (2006.01) |
| *G06T 7/00* | (2006.01) |
| *A61B 6/03* | (2006.01) |
| *G06T 17/00* | (2006.01) |
| *A61B 6/00* | (2006.01) |
| *A61B 6/12* | (2006.01) |

(52) U.S. Cl.
CPC ............... *A61B 6/032* (2013.01); *A61B 6/4014* (2013.01); *A61B 6/481* (2013.01); *G06T 2207/30101* (2013.01); *A61B 6/12* (2013.01); *G06T 7/0032* (2013.01); *A61B 6/4435* (2013.01); *G06T 2207/10072* (2013.01); *A61B 6/037* (2013.01); *A61B 6/504* (2013.01); *G06T 2207/30172* (2013.01); *G06T 17/00* (2013.01); *A61B 6/5229* (2013.01); *G06T 7/0083* (2013.01)

USPC .......................................................... 382/128

(58) Field of Classification Search
None
See application file for complete search history.

(56) References Cited

U.S. PATENT DOCUMENTS

| | | | |
|---|---|---|---|
| 7,170,517 B2* | 1/2007 | Raman et al. ................ | 345/424 |
| 7,796,790 B2* | 9/2010 | McNutt et al. ............... | 382/128 |

(Continued)

FOREIGN PATENT DOCUMENTS

| | | |
|---|---|---|
| DE | 102007003260 A1 | 10/2007 |
| DE | 102008007827 A1 | 8/2009 |
| WO | WO 2009019630 A2 * | 2/2009 |

OTHER PUBLICATIONS

Nicolas Flasque, Michel Desvignes, Jean-Marc Constans, Marinette Revenu, "Acquisition, segmentation and tracking of the cerebral vascular tree on 3D magnetic resonance angiography images" Elsevier, Medima40, 2001.*

(Continued)

*Primary Examiner* — Nirav G Patel
*Assistant Examiner* — Oneal R Mistry
(74) *Attorney, Agent, or Firm* — Harness, Dickey & Pierce (57) ABSTRACT

A method and a computer system are disclosed for automatically generating a statistical vascular model of a patient group. In at least one embodiment, the method includes collecting determining patient-related vascular coordinates models from a multiplicity of vascular landmark coordinates of vascular landmarks, centerline coordinates on vessel centerlines and vessel contour coordinates on vessel contour edge profiles; determining body landmark coordinates of body landmarks; registering the vessel-related coordinates to patient-related registered vascular coordinates models; merging patient-related vascular parameter models to form at least one statistical vascular parameter model; determining the statistical parameters thereof; and saving and/or outputting the at least one statistical vascular parameter model.

23 Claims, 5 Drawing Sheets

(56) References Cited

U.S. PATENT DOCUMENTS

| | | | |
|---|---|---|---|
| 7,873,194 B2* | 1/2011 | Begelman et al. | 382/128 |
| 8,417,009 B2* | 4/2013 | Mizuno | 382/131 |
| 2002/0184470 A1* | 12/2002 | Weese et al. | 712/1 |
| 2003/0056799 A1* | 3/2003 | Young et al. | 128/922 |
| 2007/0019846 A1* | 1/2007 | Bullitt et al. | 382/128 |
| 2007/0237373 A1* | 10/2007 | Kiraly et al. | 382/128 |
| 2008/0118121 A1* | 5/2008 | Skinner et al. | 382/128 |
| 2009/0202121 A1 | 8/2009 | Fenchel et al. | |
| 2010/0061601 A1* | 3/2010 | Abramoff et al. | 382/117 |
| 2010/0254582 A1 | 10/2010 | Liu et al. | |
| 2010/0272330 A1* | 10/2010 | Pekar et al. | 382/128 |
| 2011/0093243 A1* | 4/2011 | Tawhai et al. | 703/2 |

OTHER PUBLICATIONS

Beck, T. et al., "Statistical Modeling of the Arterial Vascular Tree", Proceedings of SPIE (2011); Others; 2011.

Seifert, A. et al., "Hierarchical Parsing and Semantic Navigation of Full Body CT Data", Proceedings of SPIE. vol. 7259 (2009); Others; 2009.

Stefan Grosskopf et al., Accurate, Fast and Robust Vessel Contour Segmentation of CTA using an Adaptive Self-Learning Edge Model, Proceedings of SPIE, vol. 7259 72594D, 2009; Others; 2009.

Certified U.S. Priority document for U.S. Appl. No. 61/440,989.

\* cited by examiner

METHOD AND COMPUTER SYSTEM FOR AUTOMATICALLY GENERATING A STATISTICAL MODEL

PRIORITY STATEMENT

The present application hereby claims priority under 35 U.S.C. §119(e) to U.S. provisional patent application Ser. No. 61/440,989 filed Feb. 9, 2011, the entire contents of which are hereby incorporated herein by reference.

FIELD

At least one embodiment of the invention generally relates to a method for automatically generating a statistical model, i.e. a model that is based on statistically analyzed measurement data and a generalized description of the measurement data that is derived therefrom, of the geometry of vascular structures of a patient group, and/or a computer system comprising programs for performing the method.

BACKGROUND

In the context of imaging methods in the field of medicine, it is customary to extract tomographical image information of a patient, in order therefrom to obtain knowledge relating to physiological conditions of the patient under examination, and to make this knowledge available to a doctor for diagnostic purposes. In the case of CT angiography, for example, a 3D data record of a vascular system is generated after dosage of a contrast medium, thereby allowing a doctor to diagnose deformations of vessels such as stenoses or aneurysms. In principle, this diagnosis can be performed directly on the basis of the tomographical displays. For the purpose of simplification, the doctor can also be provided with e.g. a so-called CPR (Curved Planar Reformation) as an overview of a vessel of the vascular system, the CPR being based on the determination of the centerline in the image of the vessel. Using the CPR, the doctor can gain an initial overview of the state of the vessel concerned and e.g. determine the positions at which the vessel is to be measured. The measurement of a vessel on the basis of the CPR requires significantly less time than the direct assessment of the tomographical image data records.

During recent years, the quantity of data to be examined when making a diagnosis has grown continuously due to the improved temporal and spatial resolution of medical image recording systems. This should reduce the time that is required to produce the diagnosis and improve the quality of the diagnosis.

SUMMARY

At least one embodiment invention therefore addresses the problem of providing the doctor with a way of easily finding parameterized display techniques for vascular structures, wherein the techniques allow statistically meaningful standard structures to be quickly (i.e. automatically) derived from a large number of tomographical data records and displayed, wherein a standard structure that is thus obtained can easily be compared with patient-related individual displays in order to provide a doctor with a basis for a diagnostic assessment.

Advantageous developments of the invention are the subject matter of subclaims.

The inventors have recognized at least the following: The work stages that are labor-intensive and susceptible to error for the radiologist can be made easier as a result of precalculated standard views and segmentation results, thereby allowing the radiologist to concentrate on more advanced medical aspects of providing the diagnosis, by using a method that generates and represents knowledge from anatomical tree structures, in particular arterial vascular trees, on the basis of statistical data material. A distinction is made between topological characteristics and geometrical characteristics. The topology describes the structure, i.e. which vessel sections are connected together via which paths, for example. By contrast, the geometry merely describes the shape of the structures, e.g. the direction, curvature, diameter and length of the vessel section.

The background anatomical knowledge that is used here, and can be generated and represented using the proposed statistical geometrical model, provides a central foundation for the fully automatic extraction and examination of the arterial vascular tree in this case. In addition to the vessel-specific parameterization of the segmentation algorithms and the detection of vascular landmarks, the scope of application also includes the application as an anatomical reference for the identification of pathological changes.

It is proposed that a statistical geometrical model be created on the basis of a combination of location probabilities of normal distributions of vascular landmarks and parameterized characteristics of the vascular connections between the landmarks, including parameterized vascular characteristics at predefined relative positions, wherein the statistical model is created by merging a large number of patient-specific models that correspond to the statistical model and were previously extracted from tomographical image data records. Such geometrical models are based on a general description of the vascular topology, this consisting of landmarks and unbranched vessel sections. The geometrical models are registered to each other in a non-rigid manner, thereby compensating for anatomical variations such as body size, weight, age and minor differences in the vascular tree, for example, and external parameters such as patient orientation and position on the table, for example. The patient-related registered geometrical models are merged and outliers are discarded. In the case of one-dimensional parameters such as vessel length, diameter, circumference, etc., the identification of outliers is based on a criterion using the MAD (Median Absolute Deviation). In the case of three-dimensional random variables, e.g. 3D coordinates of the landmark position, use is made of a criterion that is based on the Mahalanobis distance.

The geometrical models can therefore include, for example, the probability distributions for the coordinates of the landmarks, parameters relating to the vessel centerline sections between two landmarks, and associated parameters relating to vessel cross sections as a function of distances that are relativized over the total length of the respective vessel centerline section.

In accordance with at least one embodiment, the inventors propose a method, in its general form, for automatically generating a statistical vascular model of a patient group, the method comprising:

collecting tomographical image data records of vascular structures of the patient group, determining patient-related vascular coordinates models comprising a multiplicity of vascular landmark coordinates of vascular landmarks, centerline coordinates on vessel centerlines and vessel contour coordinates on vessel contour edge profiles, determining body landmark coordinates of body landmarks, registering the vessel-related coordinates, using the body landmarks, to patient-related registered vascular coordinates models, determining patient-related vascular parameter models from vascular landmark coordinates, neighborhood relationships of the vascular landmarks (including branchings), characteristic geometrical parameters for describing the vessel centerlines, and the shape of the vessel contour as a function of a relative distance from a vascular landmark, merging the patient-related vascular parameter models to form at least one statistical vascular parameter model and determining the statistical parameters thereof, storing and/or outputting the statistical vascular parameter model.

Specifically, the method for automatically generating a statistical model (i.e. a generalized description of measurement data, wherein said description is based on statistically analyzed measurement data) of the geometry of vascular structures of a patient group is described by the following method steps:

collecting a multiplicity of tomographical image data records of the patient group, wherein said data records collectively offer multiple coverage of an anatomical region to be observed and represent the vascular structures of the patients, determining a vascular coordinates model for each patient from the tomographical image data records by means of:
  determining vascular landmarks and their vascular landmark coordinates,
  determining the neighborhood relationships of the vascular landmarks (including branchings that are determined thereby), i.e. which landmarks are neighbors of which,
  determining unbranched vessel centerlines between two vascular landmarks in each case, and determining a multiplicity of centerline coordinates on the vessel centerlines,
  determining vessel contour edge profiles at cross sections orthogonal to the vessel centerline, and determining a multiplicity of vessel contour coordinates on the vessel contour edge profiles as a function of a relative distance (=distance relative to the total length of the vessel centerline) from a vascular landmark on the relevant vessel centerline,
  determining body landmarks in the tomographical image data records, and determining the body landmark coordinates of the body landmarks,
  registering exclusively the coordinates (=vascular landmark coordinates+centerline coordinates+vessel contour coordinates) of the patient-related vascular coordinates models, using exclusively the body landmarks as spatial reference points of the registration, to a multiplicity of patient-related registered vascular coordinates models,
  determining patient-related vascular parameter models, in each case by means of:
  using the registered vascular landmark coordinates,
  using the neighborhood relationships of the vascular landmarks (including branchings),
  determining characteristic geometrical parameters for describing (in an underspecified or complete manner) the profile of the vessel centerlines,
  determining characteristic geometrical parameters for describing (in an underspecified or complete manner) the shape of the vessel contour as a function of a relative distance (=distance relative to total length of the vessel centerline) from a vascular landmark on the relevant vessel centerline, merging the patient-related vascular parameter models to form at least one statistical vascular parameter model, and determining its statistical parameters for the probability distribution of the coordinates and parameters contained therein, storing and/or outputting the statistical vascular parameter model.

After generation of a first statistical vascular parameter model, provision is advantageously made in this case for outliers, i.e. values that come from the patient-related models but lie outside of a predetermined statistical confidence range, to be determined in the underlying patient-related vascular parameter models, to be eliminated from the patient-related vascular parameter models, and for a definitive statistical vascular parameter model to be calculated using the corrected patient-related vascular parameter models.

For the purpose of registration, the patient-related vascular coordinates models can preferably be registered in each case to a reference model that has been provided. Alternatively, however, a reference model can also be generated by way of averaging, e.g. from the totality of the relevant patient-related data, and then used. Likewise, use can arbitrarily be made of a patient-related model representing the entire vascular structure.

For the purpose of registration, it is also possible to use an algorithm for nonlinear approximation, in particular for interpolation, said algorithm being based on radial basis functions and being in particular a "3D thin-plate spline interpolation" algorithm.

For the purpose of merging the vascular landmark coordinates, it is proposed to use a three-dimensional Gaussian normal distribution.

For the purpose of identifying outliers in relation to the spatial coordinates of the vascular landmark coordinates, it is proposed to determine a probability ellipsoid for each vascular landmark and to consider the coordinates outside of the ellipsoid as outliers.

At least one parameter from the following list can advantageously be used as a characteristic parameter of the vessel centerlines:
  total length of the vessel centerline,
  value of the curvature with reference to the relative distance from a vascular landmark,
  absolute value of the curvature with reference to the relative distance from a vascular landmark,
  orientation of a tangent to the curvature with reference to the relative distance from a vascular landmark.

For the purpose of merging the characteristic parameters of the vessel centerlines, a one-dimensional Gaussian normal distribution can be assumed correspondingly for each parameter and for each relative distance.

For the purpose of identifying outliers in relation to the characteristic parameters of the vessel centerlines, a specification of the MAD (Median Absolute Deviation) can be performed.

Furthermore, at least one parameter from the following list can be used as a characteristic parameter of the vessel contour:
  smallest and greatest distance, geometrically or numerically or in terms of distance, of registered vessel contour coordinates lying opposite each other on the contour line,
  length of the registered vessel contour,
  enclosed surface area of the registered vessel contour,
  diameter or radius of the largest internal circle that can be inserted into the registered vessel contour,
  diameter or radius of the smallest encompassing external circle around the registered vessel contour.

For the purpose of merging the characteristic parameters of the vessel contour, a one-dimensional normal distribution can be assumed for each parameter and for each relative distance.

Outliers in relation to the characteristic parameters of the vessel contour can be identified after determination of the MAD.

The method described above can be used to identify a statistically relevant norm-variant of the vascular structure of a patient with the aid of tomographical image data records by performing at least the following:

using a statistical vascular parameter model which has been determined and stored according to one of the preceding method steps, determining a patient-related vascular coordinates model, and registration on the basis of identical body landmarks, determining a patient-related vascular parameter model on the basis of the identical characteristic parameters, comparing the registered patient-related vascular parameter model and the statistical vascular parameter model, outputting statistically significant deviations of the parameters of the patient-related vascular parameter model from the parameters of the statistical vascular parameter model.

In this case, the output of the statistically relevant deviations can be effected by displaying the patient-related vascular coordinates model and marking the coordinate regions of the parameters that deviate significantly.

Alternatively, the output of the statistically relevant deviations can also be effected by displaying a tomographical image data record of the patient and marking the coordinate regions of the parameters that deviate significantly.

Finally, the inventors also propose, in at least one embodiment, a computer system (in particular a tomography system) for image analysis, wherein said computer system comprises a memory for computer programs, and wherein said memory also contains computer programs which, during operation, execute the features of at least one embodiment of the inventive method described above.

BRIEF DESCRIPTION OF THE DRAWINGS

Embodiments of the invention is described in greater detail below with reference to the figures, wherein only those features that are required for an understanding of the invention are shown. The following reference signs are used: A: vascular structure; A1-A4: method steps for application of the statistical vascular model; C1: CT system; C2: first X-ray tube; C3: first detector; C4: second X-ray tube; C5: second detector; C6: gantry housing; C8: examination couch; C9: system axis; C10: controlling and computing unit; C11: contrast medium applicator; F1-F3: cross-sectional surfaces; GL1-GL17: vascular landmarks; KL1-KL6: body landmarks; M: centerline; M1: magnetic resonance tomography system; M2: magnetic coil; M3: receiver coil; M4: magnetic coil; M6: housing; M10: controlling and computing unit; P: patient; $Prg_1$-$Prg_n$: computer programs; Q1-Q3: cross sections; S1-S7: method steps for producing the statistical vascular model; Sp: vascular model.

DETAILED DESCRIPTION OF THE EXAMPLE EMBODIMENTS

While example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments will be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

Figure 1:
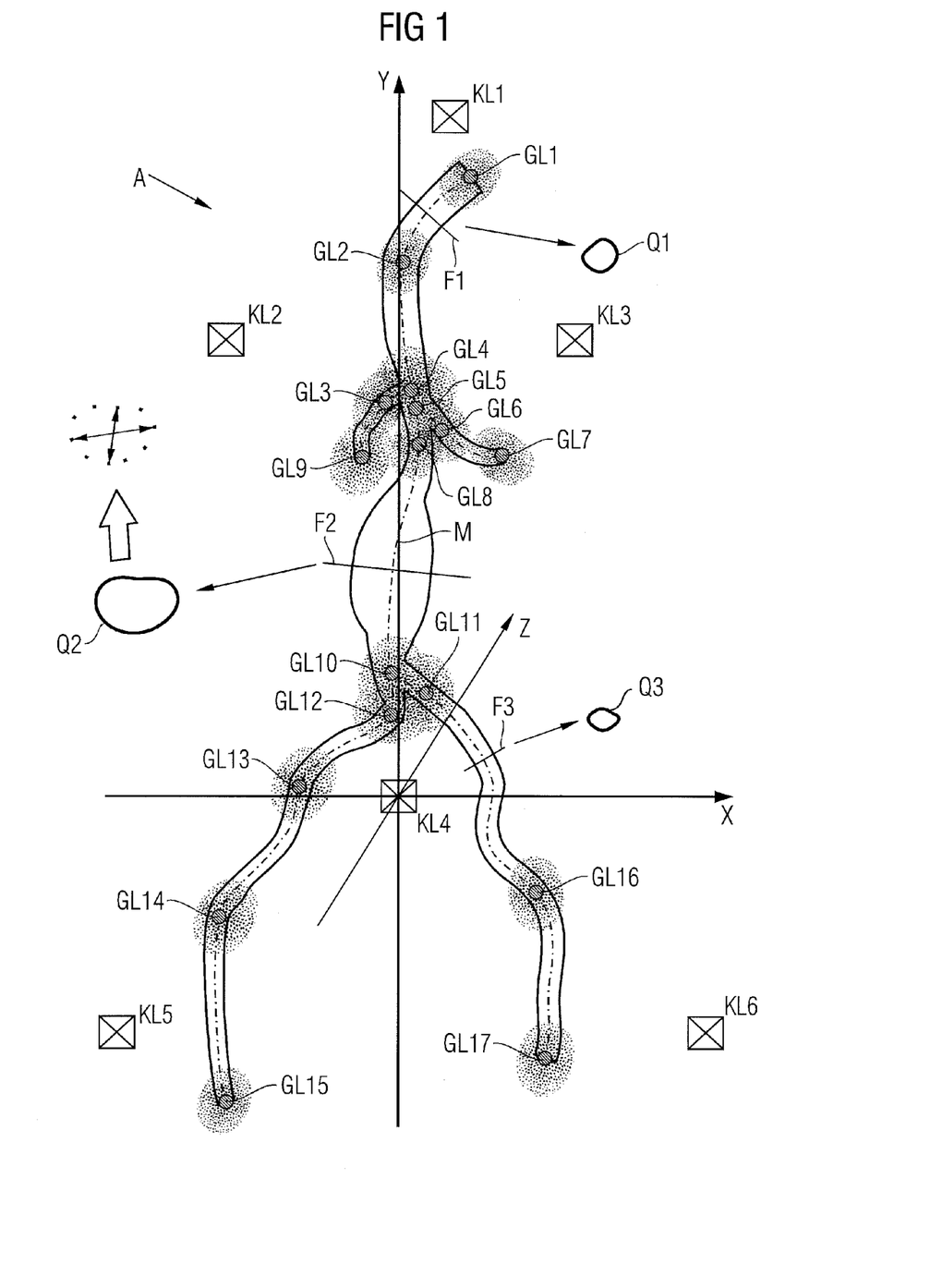
FIG. 1 shows a schematic display of a vascular structure, including parameterization as per an embodiment of the invention.

FIG. 1 shows a schematic display of an arterial vascular structure A, which has been extracted e.g. from a tomographical 3D recording of a CT examination while a contrast medium was present in the blood circulatory system. In order to explain the model that is used in the context of the invention, the essential examination criteria of said model are marked schematically. The display therefore first shows the body landmarks (=landmarks in the body of the patient under examination) KL1-KL6 that are determined for spatial orientation in the 3D display, wherein said body landmarks are determined e.g. by way of automatic or manual identification of typical bone structures of the patient under examination. These body landmarks KL1-KL6 form the spatial framework on which a plurality of patient-specific vascular structures are registered, thereby ensuring standardization of the parameters that are to be obtained.

The illustrated vascular structure A also comprises distinctive vascular landmarks (landmarks of typical positions in the vascular structure) GL1-GL17 in the form of black circles. By virtue of the examinations that are conducted according to the invention in a patient group, the location probability of these vascular landmarks GL1-GL17 can be determined from the multiplicity of examinations. The location probabilities are represented in the form of clouds of dots around the respective vascular landmarks.

In addition, a dash-dot line is drawn in the center of the profile of the vascular structure A, the line being intended to represent the centerline M in the vascular structure A. Therefore the vascular structure can now be described using neighborhood relationships of the vascular landmarks GL1-GL17, branchings (defined by a triplet of vascular landmarks in each case), and unbranched distances between pairs of vascular landmarks along the centerline M.

According to an embodiment of the invention, the profile of vessel sections between two vascular landmarks is also described in the form of a parameter profile, in that (as illustrated here by way of example) parameters relating to the vascular cross section orthogonal to the centerline are determined at a plurality of relative positions of a vessel section statistically using the patient group. These parameters are intended to describe medically relevant features of the vascular cross section, while at the same time also being easy to determine by automatic methods. In the present illustration, three exemplary cross sections Q1 to Q3 are shown at the cross-sectional surfaces F1 to F3, these being orthogonal to the centerline M.

The individually illustrated cross section Q2 is used to show—as characterized by the arrow situated above it—how typical parameters can be determined in a manner that is easy to automate, for example. According to this, the external contour line of the cross-sectional surface area is divided into a number of equidistant points on the contour line. There are ten points in the example. The distances between numerically opposite points (i.e. the first and sixth, the second and seventh, etc.) are then determined, and the maximal and minimal distances in the relevant cross section are used as parameters.

Such parameters can now be determined along the individual sections of the centerline at a multiplicity of identical relative positions of the section concerned, e.g. at every 10% of the total distance. It is therefore possible at each unbranched section between two vascular landmarks to obtain typical parameters which can easily be analyzed statistically and can therefore readily be combined to form a statistical vascular model, i.e. a generalized description of the measurement data which describes the geometry of the vascular structures of a patient group and is based on statistically analyzed measurement data.

Figure 2:
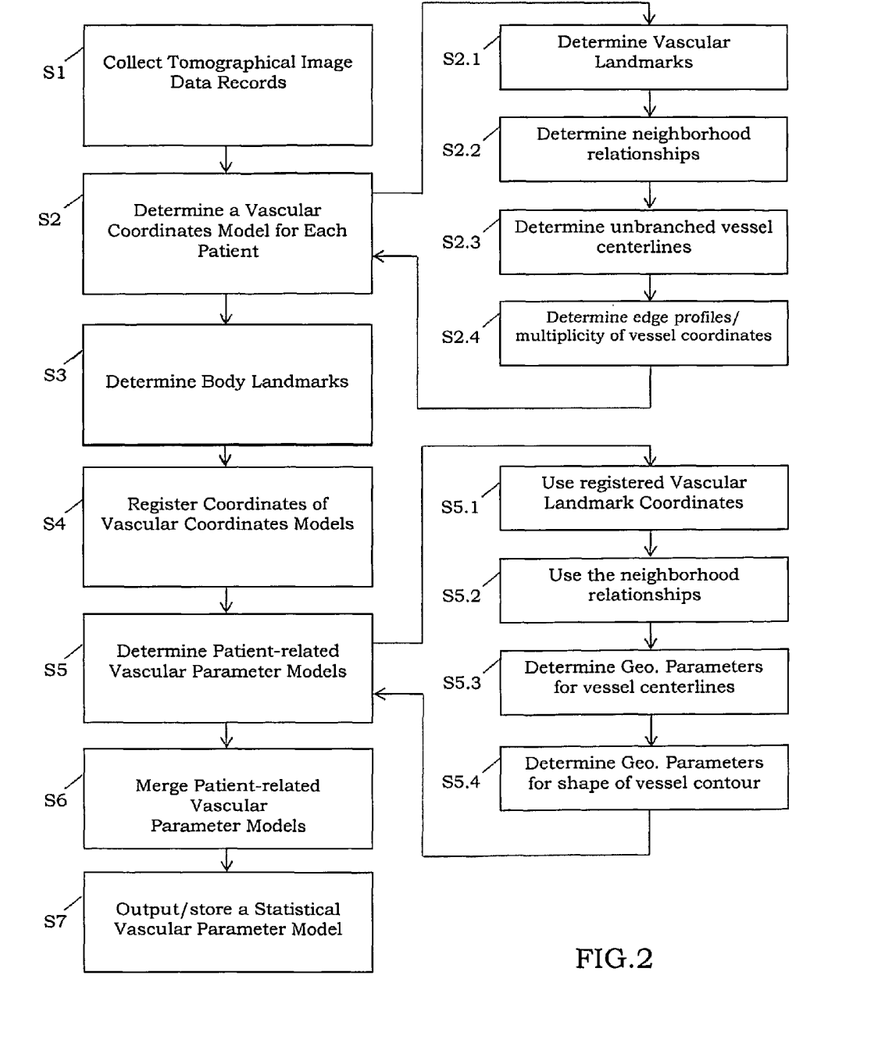
FIG. 2 shows an example flowchart of an embodiment of the inventive method for automatically generating a statistical vascular model of a patient group.

An example execution of the method for producing such a statistical vascular model is illustrated in greater detail in FIG. 2 with reference to the method steps S1 to S7.

Firstly, the method step S1 provides for collecting a multiplicity of tomographical image data records on the basis of a patient group which is optionally comparable to the greatest extent possible. In this case, it can be advantageous to select exclusively male or female patients of comparable age within a group, for example. In this case, the available examination data must collectively provide statistically meaningful coverage of an anatomical region to be observed. In principle, it is desirable in each case to use tomographical data records which completely cover the region to be observed. However, it is also possible to reproduce the entire vascular structure in a type of patchwork consisting of a sufficiently large number of overlapping partial regions, which together cover the whole of the region to be observed.

Following thereupon, the step S2 provides for determining a vascular coordinates model for each patient on the basis of the available tomographical image data records, wherein provision is preferably made for executing the following steps in particular:

S2.1: determining vascular landmarks and their vascular landmark coordinates;
S2.2: determining the neighborhood relationships of the vascular landmarks, wherein each vascular landmark is assigned a neighbor and branchings are determined as triplets of vascular landmarks;
S2.3: determining unbranched vessel centerlines between two vascular landmarks in each case, and determining a multiplicity of centerline coordinates on the vessel centerlines, wherein advantageously these centerline coordinates already determine the positions of identical relative distances between the vascular landmarks of the respective vessel section;
S2.4: determining vessel contour edge profiles at cross sections orthogonal to the vessel centerline, and determining a multiplicity of vessel contour coordinates on the vessel contour edge profiles as a function of a relative distance from a vascular landmark on the relevant vessel centerline. The relative distance in this case is considered to be the relative distance of the observed point from a vascular landmark, relative to the total length of the vessel centerline of the vessel section concerned.

In method step S3, provision is further made for determining body landmarks in the tomographical image data records, and determining the body landmark coordinates of the body landmarks. Following thereupon, the method step S4 provides for registering exclusively the coordinates (i.e. the vascular landmark coordinates, the centerline coordinates and the vessel contour coordinates) of the patient-related vascular coordinates models, using exclusively the body landmarks as spatial reference points of the registration, to a multiplicity of patient-related registered vascular coordinates models.

In the step S5, provision is finally made for determining patient-related vascular parameter models, wherein the following method steps are preferably executed:
S5.1: using the registered vascular landmark coordinates;
S5.2: using the neighborhood relationships of the vascular landmarks (including branchings);
S5.3: determining characteristic geometrical parameters for describing (in an underspecified or complete manner) the profile of the vessel centerlines;
S5.4: determining characteristic geometrical parameters for describing (in an underspecified or complete manner) the shape of the vessel contour as a function of a relative distance from a vascular landmark on the respective vessel centerline.

On the basis of the patient-related vascular parameter models determined in this way, it is now possible in the method step S6 to merge the patient-related vascular parameter models to form at least one statistical vascular parameter model, wherein provision is also made for determining the statistical parameters for probability distribution of the coordinates and parameters contained therein.

The statistical vascular parameter model is then stored and/or output in the step S7.

Such statistical vascular models can then form the basis of further examinations on patients who are comparable with the examined patient group.

Figure 3:
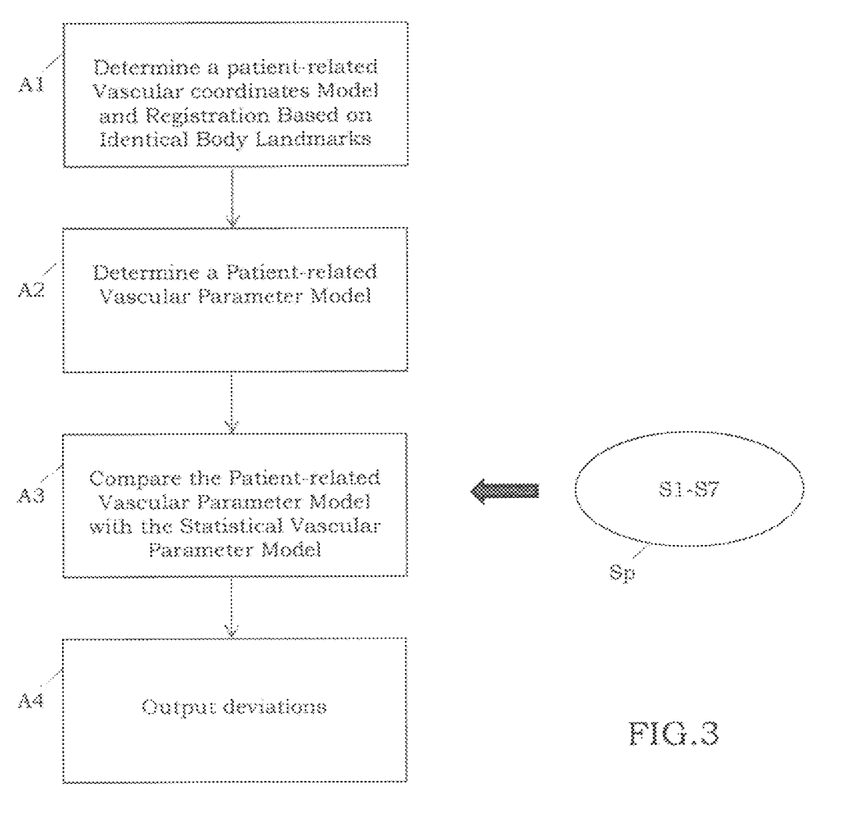
FIG. 3 shows an example flowchart of the application of an embodiment of the inventive method for automatically generating a statistical vascular model of a patient group.

An example flowchart of the application of the inventive method for automatically generating a statistical vascular model of a patient group, as described with reference to FIG. 2, is illustrated in FIG. 3 using the method steps A1 to A4.

Accordingly, determination of a patient-related vascular coordinates model and registration on the basis of identical body landmarks are performed in the first method step A1, wherein fundamentally the same patient-related methods are used for this purpose as were performed when determining the patient-related vascular models for the purpose of calculating a statistical vascular model, e.g. in accordance with the method as per FIG. 2. Following thereupon, the step A2 provides for determining a patient-related vascular parameter model on the basis of the identical characteristic parameters.

In the step A3, the statistical vascular model Sp which was previously stored by way of the steps S1-S7 described above is used for comparison with the registered patient-related vascular parameter model, and statistically significant deviations in the parameters of the patient-related vascular parameter model from the parameters of the statistical vascular parameter model are output in the step A4.

Such an output can be purely numerical, in the form of a list detailing the statistically relevant parameter deviations, wherein a graphical representation of the statistical confidence ranges with the actual patient-related parameters marked therein can also be used for this purpose. Alternatively, the magnitude of the parameter deviations can be shown in conjunction with a view of the vascular structure by way of variously configured colored markings in a tomographical display.

In principle, the method described above can be performed in conjunction with any type of tomographical display depicting vascular structures of patients. In particular, CT, PET, SPECT and MRT displays are suitable for this purpose. A CT system and an MRT system are described in the FIGS. 4 and 5 as examples of tomography systems that are used particularly frequently.

Figure 4:
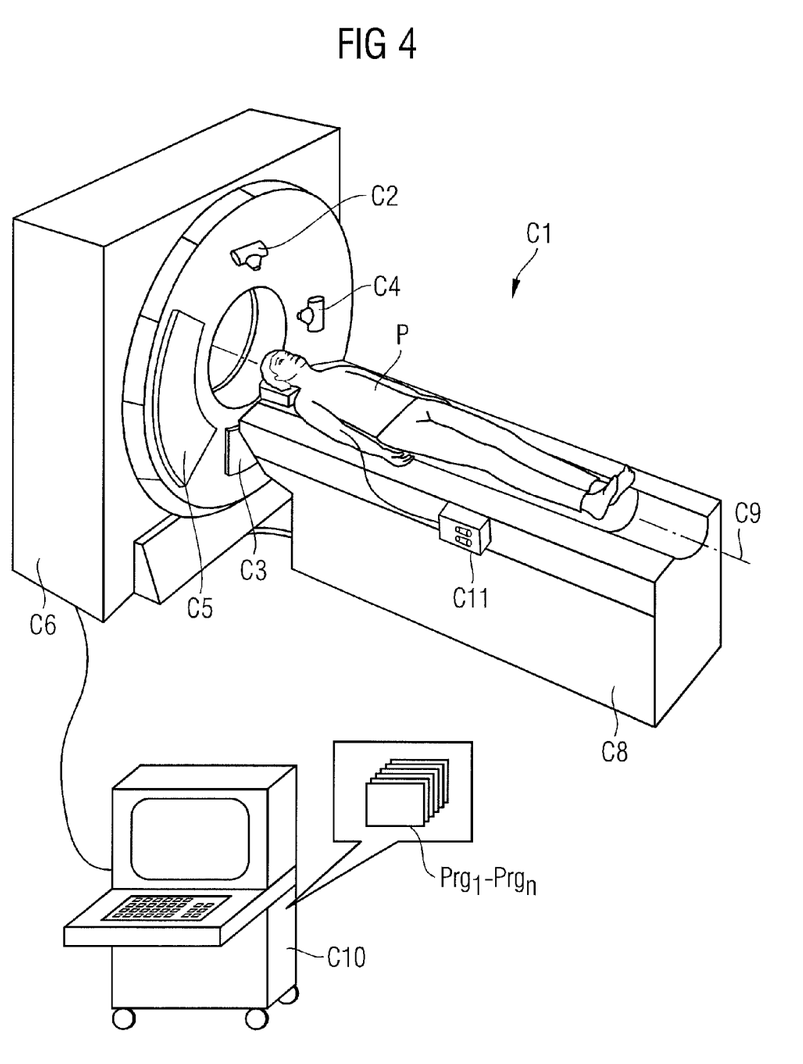
FIG. 4 shows a CT system for carrying out an embodiment of the method.

FIG. 4 shows a CT system C1 in which the inventive method can be performed. The CT system C1 features a first tube/detector system comprising an X-ray tube C2 and a detector C3 which is situated opposite thereto. This CT system C1 can optionally feature a second X-ray tube C4 and a detector C5 which is situated opposite thereto. Both tube/detector systems are located on a gantry which is arranged in a gantry housing C6 and rotates about a system axis C9 during the scan. The patient P is located on a movable examination couch C8, which is moved either continuously or sequentially along the system axis C9 through the scanning field in the gantry housing C6, wherein the attenuation of the X-radiation emitted by the X-ray tubes is measured by the detectors.

By way of a contrast medium applicator C11, the patient P can be injected with a contrast medium bolus during the measurement in order that the blood vessels are easier to recognize.

Control of the CT system C1 is coordinated by way of a controlling and computing unit C10, which also contains computer programs $Prg_1$ to $Prg_n$ that can perform the inventive method described above. The storage and output of the result data can also be effected by way of this controlling and computing unit C10.

Figure 5:
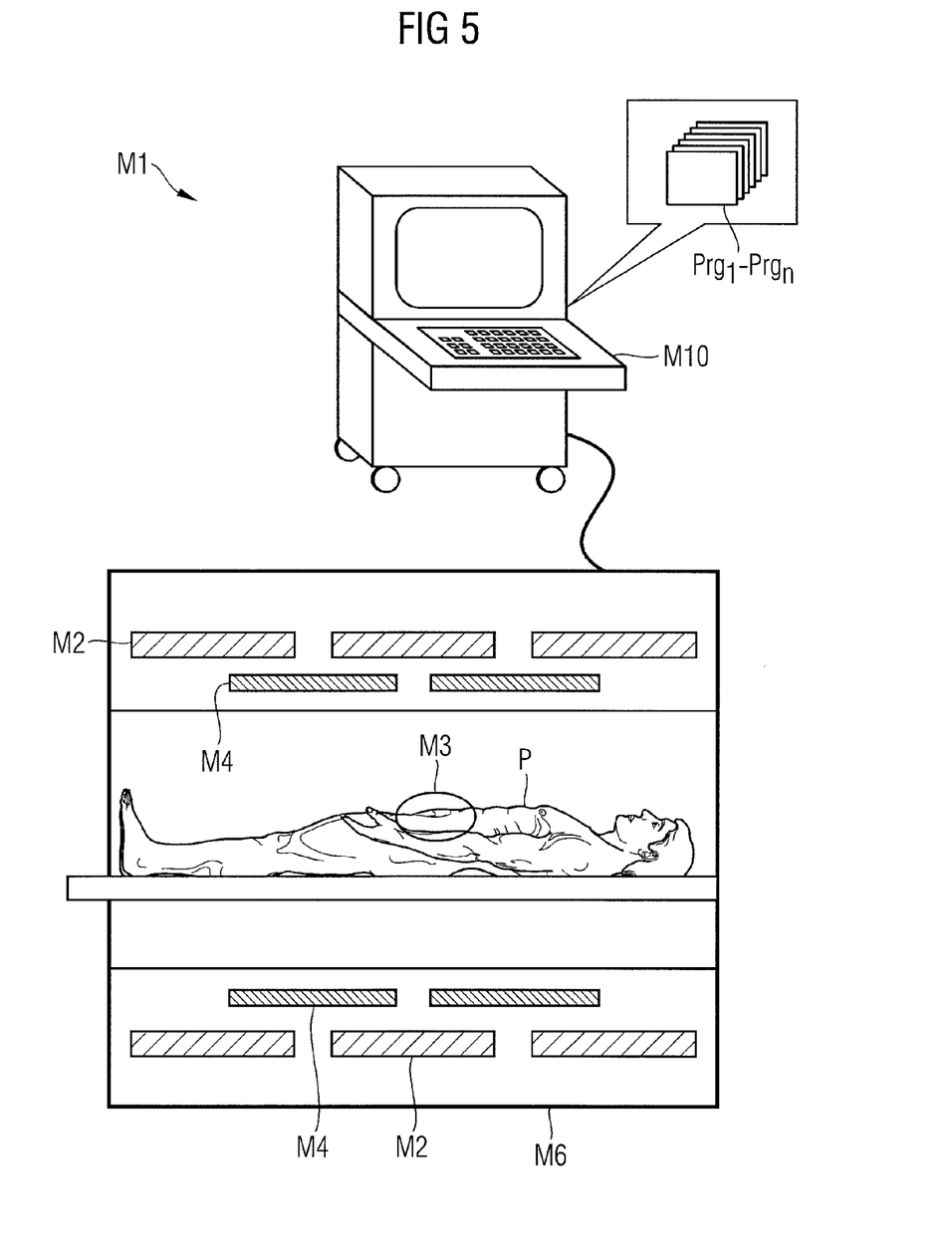
FIG. 5 shows an MRT system for carrying out an embodiment of the method.

Lastly, FIG. 5 schematically illustrates a magnetic resonance tomography system (MRT system) M1. This MRT system M1 comprises a housing M6 in which are located a plurality of magnetic coils M2 for generating a strong magnetic main field, whereby the hydrogen nuclei in the body of the patient P align themselves parallel or anti-parallel with the magnetic field lines depending on their spin. As a result of exciting the atomic nuclei using an electromagnetic alternating field in the resonance frequency of the atomic nuclei, these are caused to vibrate. After the excitation frequency is switched off, the atomic nuclei return to their positions and release their vibrational energy in the form of electromagnetic vibrational energy which is measured by receiver coils M3. Using additional magnetic coils M4, a weak magnetic field having a defined field gradient is generated, whereby the signals emitted by the nuclei are given location information by means of which the position of the emitted signal can be defined. A spatial tomographical representation of the patient P can therefore be generated. The control of this system M1 and the analysis of the measured signals are performed by the controlling and computing unit M10, whose memory also contains programs $Prg_1$ to $Prg_n$ that can execute the inventive method in addition to performing the control and image computation. However, it should be noted that a computer system according to an embodiment of the invention does not necessarily have to be directly connected to a tomography system, and the method according to an embodiment of the invention can also be performed autonomously on the basis of existing measurement data or previously prepared tomographical data records.

In summary, an embodiment of the invention therefore proposes a method for automatically generating a statistical vascular model of a patient group, said method comprising the method steps:

collecting tomographical image data records of vascular structures of the patient group, determining patient-related vascular coordinates models from a multiplicity of vascular landmark coordinates of vascular landmarks, centerline coordinates on vessel centerlines and vessel contour coordinates on vessel contour edge profiles, determining body landmark coordinates of body landmarks, registering the vessel-related coordinates, using the body landmarks, to patient-related registered vascular coordinates models, determining patient-related vascular parameter models from vascular landmark coordinates, neighborhood relationships of the vascular landmarks (including branchings), characteristic geometrical parameters for describing the vessel centerlines, and the shape of the vessel contour as a function of a relative distance from a vascular landmark, merging the patient-related vascular parameter models, and determining statistical parameters, storing and/or outputting the statistical vascular parameter model.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail with reference to the preferred exemplary embodiment, the invention is not restricted by the disclosed examples, and other variations can be derived therefrom by a person skilled in the art without thereby departing from the scope of the invention.

What is claimed is:

1. A method for automatically generating a statistical vascular model of a patient group, the method comprising:
    collecting tomographical image data records of vascular structures of the patient group;
    determining patient-related vascular coordinates models from a multiplicity of vascular landmark coordinates of vascular landmarks, centerline coordinates on vessel centerlines and vessel contour coordinates on vessel contour edge profiles;
    determining body landmark coordinates of body landmarks;
    registering the vascular landmark coordinates, the centerline coordinates and the vessel contour coordinates, using the body landmarks, to patient-related registered vascular coordinates models;
    determining patient-related vascular parameter models from the vascular landmark coordinates, neighborhood relationships of the vascular landmarks, characteristic geometrical parameters describing the vessel centerlines, and a shape of a vessel contour as a function of a relative distance from a given one of the vascular landmarks;
    merging the patient-related vascular parameter models to form at least one statistical vascular parameter model,
    determining statistical parameters of the at least one statistical vascular parameter model; and
    at least one of saving and outputting the at least one statistical vascular parameter model.

2. The method as claimed in claim 1, wherein, the registering registers the patient-related vascular coordinates models to a reference model.

3. The method as claimed in claim 2, wherein, the registering registers the patient-related vascular coordinates according to an algorithm for nonlinear approximation, said algorithm being based on a radial basis function.

4. The method as claimed in claim 3, wherein the algorithm is a "3D thin-plate spline interpolation" algorithm.

5. The method as claimed in claim 1, wherein the merging the patient-related vascular parameter models includes merging the vascular landmark coordinates based on a three-dimensional normal distribution.

6. The method as claimed in claim 1, wherein at least one of the following parameters is used as a characteristic parameter of the vessel centerlines:
    total length of the vessel centerline,
    value of the curvature with reference to the relative distance from a vascular landmark,
    absolute value of the curvature with reference to the relative distance from a vascular landmark, and
    orientation of a tangent to the curvature with reference to the relative distance from a vascular landmark.

7. The method as claimed in claim 1, wherein the merging the patient-related vascular parameter models includes merging the characteristic geometrical parameters of the vessel centerlines based on a one-dimensional normal distribution for each of the characteristic geometrical parameters and a relative distance of each of the characteristic geometrical parameters from one of the vascular landmarks on a corresponding one of the vessel centerlines.

8. The method as claimed in claim 1, wherein at least one of the following parameters is used as a characteristic parameter of the vessel contour:
    relatively smallest and relatively greatest distance, geometrically or numerically or in terms of distance, of registered vessel contour coordinates lying opposite each other on the contour line,
    length of the registered vessel contour,
    enclosed surface area of the registered vessel contour,
    diameter/radius of the relatively largest internal circle that is insertable into the registered vessel contour, and
    diameter/radius of the relatively smallest encompassing external circle around the registered vessel contour.

9. The method as claimed in claim 1, wherein the merging the patient-related vascular parameter models includes merging the characteristic geometrical parameters of the vessel contour, based on a one-dimensional normal distribution for each of the characteristic geometrical parameters and a relative distance a relative distance of each of the characteristic geometrical parameters from one of the vascular landmarks on a corresponding one of the vessel centerlines.

10. A computer system for image analysis, comprising: a memory storing computer programs which, during operation, execute the method of claim 1.

11. The system of claim 10, wherein the system is a tomography system.

12. A non-transitory computer readable medium including program segments for, when executed on a computer device, causing the computer device to implement the method of claim 1.

13. A method for automatically generating a statistical model of a geometry of vascular structures of a patient group, comprising:
    collecting a multiplicity of tomographical image data records of the patient group, wherein said tomographical image data records collectively offer multiple coverage of an anatomical region to be observed and represent the vascular structures of patients of the patient group;
    determining a vascular coordinates model for each of the patients from the tomographical image data records by way of at least one of:
    determining vascular landmarks and corresponding vascular landmark coordinates,
    determining neighborhood relationships of the vascular landmarks,
    determining unbranched vessel centerlines between two of the vascular landmarks in each case,
    determining a multiplicity of centerline coordinates on the determined unbranched vessel centerlines, determining vessel contour edge profiles at cross sections orthogonal to the determined unbranched vessel centerlines, and determining a multiplicity of vessel contour coordinates on the vessel contour edge profiles as a function of a relative distance from a given one of the vascular landmarks on a corresponding one of the vessel centerlines;

determining body landmarks in the tomographical image data records;

determining body landmark coordinates of the determined body landmarks;

registering exclusively coordinates of the patient-related vascular coordinates models, using exclusively the body landmarks as spatial reference points for the registering, to a multiplicity of patient-related registered vascular coordinates models;

determining patient-related vascular parameter models, in each case by way of at least one of:

using the registered vascular landmark coordinates, using the neighborhood relationships of the vascular landmarks, determining characteristic geometrical parameters for describing a profile of the vessel centerlines, and determining characteristic geometrical parameters for describing a shape of the vessel contour as a function of a relative distance from a given one of the vascular landmarks on a corresponding one of the vessel centerlines;

merging the patient-related vascular parameter models to form at least one statistical vascular parameter model;

determining statistical parameters of the at least one statistical vascular parameter model for a probability distribution of coordinates and parameters contained therein; and at least one of storing and outputting the at least one statistical vascular parameter model.

14. The method as claimed in claim 13, wherein, after generation of a first statistical vascular parameter model, outliers in the underlying patient-related vascular parameter models are determined and eliminated from the patient-related vascular parameter models, and a definitive statistical vascular parameter model is calculated on the basis of the corrected patient-related vascular parameter models.

15. The method as claimed in claim 14, wherein,
the identifying identifies the outliers in relation to spatial coordinates of the vascular landmark coordinates and based on a probability ellipsoid specified for each vascular landmark, and coordinates outside of the probability ellipsoid are considered as outliers.

16. The method as claimed in claim 14, wherein the identifying identifies the outliers in relation to the characteristic geometrical parameters of the vessel centerlines, based on Median Absolute Deviation (MAD).

17. The method as claimed in claim 14, wherein the identifying identifies the outliers in relation to the characteristic geometrical parameters of the vessel contour, based on Median Absolute Deviation (MAD).

18. A non-transitory computer readable medium including program segments for, when executed on a computer device, causing the computer device to implement the method of claim 13.

19. A method for identifying a statistically relevant norm-variant of the vascular structure of a patient with the aid of tomographical image data records, the method comprising:

obtaining at least one of the at least one statistical vascular parameter model determined and stored by performing the method of claim 1;

determining a patient-related vascular coordinates model, and registration on a basis of identical body landmarks in the patient-related vascular coordinates model and the at least one obtained statistical vascular parameter model;

determining a patient-related vascular parameter model on the basis of the identical characteristic parameters;

comparing the registered patient-related vascular parameter model and the at least one obtained statistical vascular parameter model; and outputting statistically significant deviations of the parameters of the patient-related vascular parameter model from the parameters of the at least one obtained statistical vascular parameter model.

20. The method as claimed in claim 19, wherein the output of the statistically relevant significant deviations is effected by displaying the patient-related vascular coordinates model and marking the coordinate regions of the parameters that deviate significantly.

21. The method as claimed in claim 20, wherein the output of the statistically significant deviations is effected by displaying a tomographical image data record of the patient and marking the coordinate regions of the parameters that deviate significantly.

22. A computer system for image analysis, comprising:
a memory storing computer programs which, during operation, execute the method of claim 19.

23. A tangible non-transitory computer readable medium including program segments for, when executed on a computer device, causing the computer device to implement the method of claim 19.

* * * * *